US011976032B2

United States Patent
Schmitt et al.

(10) Patent No.: US 11,976,032 B2
(45) Date of Patent: May 7, 2024

(54) PROCESS FOR PREPARING S,S'-DIALKYLDITHIOCARBONATE FROM DIALKYL DISULFIDE

(71) Applicant: Arkema France, Colombes (FR)

(72) Inventors: Paul-Guillaume Schmitt, Lescar (FR); Georges Frémy, Sauveterre de Bearn (FR); Gilles-Olivier Gratien, Nantes (FR)

(73) Assignee: Arkema France, Colombes (FR)

( * ) Notice: Subject to any disclaimer, the term of this patent is extended or adjusted under 35 U.S.C. 154(b) by 847 days.

(21) Appl. No.: 16/976,336

(22) PCT Filed: Mar. 13, 2019

(86) PCT No.: PCT/EP2019/056274
§ 371 (c)(1),
(2) Date: Aug. 27, 2020

(87) PCT Pub. No.: WO2019/175235
PCT Pub. Date: Sep. 19, 2019

(65) Prior Publication Data
US 2023/0167052 A1    Jun. 1, 2023

(30) Foreign Application Priority Data

Mar. 13, 2018   (FR) .................................. 1852149

(51) Int. Cl.
*C07C 329/16* (2006.01)
*B01J 23/44* (2006.01)
*C07C 315/04* (2006.01)

(52) U.S. Cl.
CPC ............ *C07C 315/04* (2013.01); *B01J 23/44* (2013.01); *C07C 329/16* (2013.01)

(58) Field of Classification Search
CPC .................................................. C07C 329/16
See application file for complete search history.

(56) References Cited

U.S. PATENT DOCUMENTS

| 4,449,004 | A | 5/1984 | Degani et al. |
| 2007/0249620 | A1 | 10/2007 | Kurata et al. |
| 2018/0037697 | A1 | 2/2018 | Müller et al. |

FOREIGN PATENT DOCUMENTS

| EP | 0063327 A1 | 10/1982 |
| JP | 2007191471 A | 8/2007 |
| WO | 2006004200 A1 | 1/2006 |
| WO | 2006020281 A1 | 2/2006 |

OTHER PUBLICATIONS

Arisawa, M. et al., "Rhodium-catalysed alkylthio exchange reaction of thioester and disulfide," Tetrahedron Letters, vol. 49(12), 2008, pp. 1975-1978.
Basu et al., "Merox and Related Metal Phthalocyanine Catalyzed Oxidation Processes", Catalysis Reviews; Science and Engineering, vol. 35, No. 4, pp. 571-609, (Sep. 23, 2006).
International Search Report and Written Opinion for International Application No. PCT/EP2019/056274, dated May 24, 2019, with partial translation, 7 pages.

*Primary Examiner* — Bruck Kifle
(74) *Attorney, Agent, or Firm* — Buchanan Ingersoll & Rooney PC

(57) ABSTRACT

A process for preparing an S,S'-dialkyldithiocarbonate from a dialkyl disulfide and from a particular metal catalyst, in the presence of carbon monoxide is described in addition to the use of S,S'-dialkyldithiocarbonates as reagents for the preparation of polycarbonates, compounds containing at least one urea and/or isocyanate function and compounds containing at least one thioalkyl function.

10 Claims, No Drawings

PROCESS FOR PREPARING S,S'-DIALKYLDITHIOCARBONATE FROM DIALKYL DISULFIDE

CROSS-REFERENCE TO RELATED APPLICATIONS

This is the national phase of International Application No. PCT/EP2019/056274, filed 13 Mar. 2019, which claims priority to French Application No. 1852149, filed 13 Mar. 2018. The disclosure of each of these applications is incorporated herein by reference in its entirety for all purposes.

The present invention relates to a process for preparing an S,S'-dialkyldithiocarbonate from a dialkyl disulfide and from a particular metal catalyst, in the presence of carbon monoxide.

The present invention also relates to the use of at least one S,S'-dialkyldithiocarbonate as a reagent for the preparation of polycarbonates, of compounds of urea and/or isocyanate type or of compounds comprising at least one thioalkyl function.

Carbonyl dichloride, or phosgene, is a compound commonly used by the chemical industry, in particular for the synthesis of isocyanates and polycarbonates.

Despite its advantageous chemical properties, the use of phosgene remains limited because of its high toxicity. Gaseous at ambient temperature and lethal, even at low doses, its use is today highly regulated. Numerous studies thus seek to replace phosgene with other compounds which are less toxic and easier to use in industrial processes.

Recently, S,S'-dialkyldithiocarbonates have been studied for their ability to be able to replace phosgene in processes for preparing urea derivatives. Indeed, this compound has the advantage of being less toxic and less volatile than phosgene. However, the synthesis of S,S'-dialkyldithiocarbonates is particularly complex.

Several Japanese scientific publications, in particular Arisawa et al., Tetrahedron Letters, (2008), 49(12), 1975-78, have in particular described a process for synthesizing S,S'-dialkyldithiocarbonates from a dialkyl disulfide and a selenium- or rhodium-based catalyst.

However, selenium is a very toxic catalyst and rhodium-based catalysts are very expensive.

Thus, there is a real need to develop a process for preparing S,S'-dialkyldithiocarbonate which is less toxic to human beings and to the environment, easily industrializable, and optionally less expensive compared with processes using rhodium.

These aims are entirely or at least partially achieved with the present invention, a subject of which is in particular a process for preparing at least one S,S'-dialkyldithiocarbonate, comprising the following step (a):

(a) reacting in the presence of carbon monoxide:
  at least one dialkyl disulfide,
  at least one catalyst comprising at least one metal chosen from nickel, palladium and platinum, and
  optionally in the presence of a solvent or a mixture of solvents.

The applicant has in particular noted that the process according to the invention makes it possible to obtain S,S'-dialkyldithiocarbonate by carbonylation of at least one dialkyl disulfide, with a better yield than the prior art processes.

It has also been noted that the process according to the invention uses catalysts which are less toxic, and which may also be less expensive, than those used in the prior art processes.

Other features, aspects, subjects and advantages of the present invention will emerge even more clearly on reading the description and the examples which follow.

Furthermore, any range of values denoted by the expression "between a and b" represents the range of values extending from a up to b (that is to say including the strict limits of a and b).

Throughout the text, the pressures are expressed in megapascals (MPa) absolute.

Dialkyl Disulfide

Step (a) of the preparation process according to the invention reacts at least one dialkyl disulfide.

According to the invention, the dialkyl disulfide(s) may be symmetrical or asymmetrical. In other words, the two alkyl radicals of a dialkyl disulfide may be identical or different.

Preferably, the dialkyl disulfide(s) are chosen from the dialkyl disulfides of formula (I) below, and mixtures thereof:

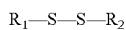

in which:

$R_1$ and $R_2$, which may be identical or different, represent a linear or branched, saturated, $C_1$-$C_{12}$, more preferentially $C_1$-$C_8$, even more preferentially $C_1$-$C_4$, hydrocarbon-based chain optionally containing one or more heteroatoms, which may be identical or different, preferably chosen from O, N and/or S.

$R_1$ and $R_2$ are preferably identical.

More preferentially, $R_1$ and $R_2$ are identical and represent a $C_1$-$C_4$ hydrocarbon-based chain, such as a methyl, ethyl, propyl, isopropyl, butyl, sec-butyl, isobutyl or tert-butyl group.

The term "identical" is intended to mean having the same number of carbon atoms, and in the same stereochemical configuration.

Even more preferentially, $R_1$ and $R_2$ each represent a methyl group.

According to one preferred embodiment of the invention, the dialkyl disulfide(s) are chosen from dimethyl disulfide, diethyl disulfide, dipropyl disulfide, dibutyl disulfide, and mixtures thereof, more preferentially from dimethyl disulfide.

By way of example, the dialkyl disulfide(s) that can be used in the process according to the invention may be a mixture of organic disulfides or DSOs (disulfide oils) originating in particular from gas or oil extraction fields.

More specifically, DSOs (disulfide oils) are mixtures of organic disulfides produced during the treatment of the mercaptans contained in petroleum fractions or liquefied gases by processes of "Merox" type (see, for example, Catal. Review—Sci. Eng., 35(4), (1993), 571-609).

Catalysts

Step (a) of the preparation process according to the invention reacts at least one catalyst comprising at least one transition metal chosen from nickel, palladium and platinum.

According to the invention, the catalyst(s) are in the form of pure metal or in the form of an organometallic complex.

Preferably, the catalyst(s) are in the form of an organometallic complex.

When the catalyst(s) are in the form of an organometallic complex, the transition metal(s) are covalently bonded with one or more ligands.

Preferably, said ligand(s) are chosen from triphenylphosphine, 1,2-bis(diphenylphosphino)ethane (or dppe), 1,5-bis(diphenylphosphino)pentane (or dpppentane), 1,1'-bis(diphenylphosphino)ferrocene (or dppf), 1,3- diisopropylimidazolium tetrafluoroborate (or IiPr$^+$.BF$_4^-$), 1,4-bis(diphenylphosphino)butane (or dppb), carbon monoxide, and mixtures thereof.

Optionally, said ligand(s) of phosphine type that can be used according to the invention, in particular those chosen from triphenylphosphine, 1,2-bis(diphenylphosphino)ethane (or dppe), 1,5-bis(diphenylphosphino)pentane (or dpppentane), 1,1'-bis(diphenylphosphino)ferrocene (or dppf) and 1,4-bis(diphenylphosphino)butane (or dppb), undergo a sulfonation reaction. Said ligand(s) of phosphine type treated by sulfonation comprise at least one sulfonate function.

The catalysts that can be used in the process according to the invention may be soluble or insoluble in the dialkyl disulfide(s) used.

The catalysts that can be used in the process according to the invention may also be in solid form, supported by a porous support chosen from $SiO_2$, $Al_2O_3$, $TiO_2$, $Al_2O_3/SiO_2$, $ZrO_2$, zeolites, carbon-based materials, and mixtures thereof.

Preferably, the catalyst(s) that can be used in the process according to the invention are soluble in the dialkyl disulfide(s) used.

Preferably, the catalyst comprising at least one nickel atom is nickel tetracarbonyl.

Preferably, the catalyst comprising at least one palladium atom is tetrakis(triphenylphosphine)palladium.

Preferably, the catalyst(s) comprising at least one platinum atom are chosen from platinum in pure metal form, tetrakis(triphenylphosphine)platinum, and mixtures thereof.

According to one preferred embodiment of the invention, the catalyst(s) that can be used in the process according to the invention are chosen from nickel tetracarbonyl, tetrakis(triphenylphosphine)palladium, platinum in pure metal form, tetrakis(triphenylphosphine)platinum, and mixtures thereof.

According to one particularly preferred embodiment of the invention, the catalyst comprises palladium; more preferentially the catalyst is tetrakis(triphenylphosphine)palladium.

Preferably, the catalyst(s) that can be used in the process according to the invention have an oxidation state 0, or an oxidation state +2 or (II).

Preferably, the number of moles of catalyst(s) introduced into the reaction of step (a) is between 0.1 and 3 mol %, more preferentially between 0.5 and 2.5 mol %, even more preferentially between 0.5 and 2 mol %, relative to the total number of moles of dialkyl disulfide(s) introduced into the reaction of step (a).

The number of moles of catalyst is calculated by dividing the weight of the catalyst measured by weighing, by the molar mass of the catalyst.

Carbon Monoxide

Step (a) of the preparation process according to the invention is carried out in the presence of carbon monoxide.

Preferably, the reaction according to step (a) of the process according to the invention is carried out under a total carbon monoxide pressure of between 1 and 20 MPa, more preferentially between 3 and 15 MPa, even more preferentially between 4 and 8 MPa.

Additional Ligand

Step (a) of the preparation process according to the invention may optionally comprise the addition, to the reaction medium, of at least one additional ligand.

For the purposes of the present invention, an additional ligand is an organic molecule which, once introduced into the reaction medium of the reaction of step (a), can optionally covalently bond to a metal or to an organometallic complex.

For the purposes of the invention, it is understood that the chemical structure of the additional ligand(s) may be identical to the chemical structure of the ligand(s) of the catalyst(s). For the purposes of the invention, it is also understood that the additional ligand(s) are added to the reaction medium as reagents, distinct from the catalyst(s).

Preferably, the additional ligand(s) are chosen from triphenylphosphine, 1,2-bis(diphenylphosphino)ethane (or dppe), 1,5-bis(diphenylphosphino)pentane (or dpppentane), 1,1'-bis(diphenylphosphino)ferrocene (or dppf), 1,3-diisopropylimidazolium tetrafluoroborate (or IiPr$^+$.BF$_4^-$), 1,4-bis(diphenylphosphino)butane (or dppb), carbon monoxide, and mixtures thereof.

Preferably, when the additional ligand(s) are reacted in step (a) of the process according to the invention, the number of moles of additional ligand(s) introduced is between 0.1 and 6 mol %, more preferentially between 0.3 and 5 mol %, even more preferentially between 0.5 and 4 mol %, relative to the total number of moles of dialkyl disulfide(s) introduced into the reaction of step (a).

Solvents

A solvent or a mixture of solvents may optionally be used in the reaction according to step (a).

According to one particular embodiment of the invention, the reaction according to step (a) can be carried out in the dialkyl disulfide(s), such as dimethyl disulfide (DMDS), which will act both as reaction solvent and as reagent.

By way of example, the solvent(s) can be chosen from aprotic solvents and/or protic solvents.

According to another particular embodiment of the invention, step (a) of the process according to the invention uses toluene or 2-ethylhexyl acetate as reaction solvent.

Reaction Conditions

Step (a) according to the invention can be carried out at a temperature ranging from 70 to 200° C., preferably from 90 to 180° C., more preferentially from 100 to 170° C., even more preferentially from 100 to 160° C.

Preferably, the duration of step (a) ranges from a few minutes to several hours, preferentially from 5 minutes to 72 hours, more preferentially from 10 minutes to 60 hours, even more preferentially from 10 minutes to 45 hours.

By way of example, the reaction can take place in fixed bed tubular, multitubular, catalytic wall microchannel or fluidized bed reactors.

A subject of the invention is also the use of at least one S,S'-dialkyldithiocarbonate obtained by means of a process as described above, as a reagent for the preparation of polycarbonates or of compounds comprising at least one urea and/or isocyanate function.

Preferably, the invention relates to the use of at least one S,S'-dialkyldithiocarbonate obtained by means of a process as described above, as a reagent for the preparation of polycarbonates or of compounds comprising at least one urea and/or isocyanate function.

A subject of the invention is also the use of at least one S,S'-dialkyldithiocarbonate obtained by means of a process as described above, as a reagent for the preparation of compounds comprising at least one thioalkyl function (i.e. an —S-alkyl, preferably $C_1$-$C_6$ alkyl, function), more preferentially a thiomethyl function (i.e. an —S—$CH_3$ function).

The preparation of polycarbonates or of compounds comprising at least one urea and/or isocyanate function according to the invention comprises:

1) a first step of preparing at least one S,S'-dialkyldithiocarbonate according to the process of the invention as described above, and
2) a second step of preparing polycarbonates or compounds comprising at least one urea and/or isocyanate function, from S,S'-dialkyldithiocarbonate obtained by means of preparation step 1).

By way of examples, the second step described above for preparing compounds comprising at least one urea function from S,S'-dialkyldithiocarbonate may be identical to the preparations described in patent applications ITMI 20042402, JP 2007/191471 and WO 2006/004200, with the difference that these prior preparations are carried out starting from S,S'-dialkyldithiocarbonate obtained by means of a process different from the process according to the invention.

The preparation of compounds comprising at least one thioalkyl, preferably thiomethyl, function according to the invention comprises:
1) a first step of preparing at least one S,S'-dialkyldithiocarbonate according to the process of the invention as described above, and
2) a second step of preparing compounds comprising at least one thioalkyl, preferably thiomethyl, function from S,S'-dialkyldithiocarbonate obtained by means of preparation step 1).

By way of example, the second step described above for preparing compounds comprising at least one thioalkyl function from S,S'-dialkyldithiocarbonate may be identical to the preparation described in patent application EP 0 063 327, with the difference that this prior preparation is carried out starting from S,S'-dialkyldithiocarbonate obtained by means of a process different from the process according to the invention. Thus, it is possible to obtain mercaptotriazines, used for example as herbicides, pesticides, in paints, as pharmaceutical intermediates, oxidation inhibitors or additives for lubricants.

Said S,S'-dialkyldithiocarbonate(s) used as a reagent can be prepared according to the process for preparing at least one S,S'-dialkyldithiocarbonate as described above.

The present invention will now be described in the examples below, such examples being given purely for illustrative, and obviously non-limiting, purposes.

EXAMPLES

Catalyst Evaluation

The catalysts comprising at least one transition metal are evaluated in a reaction for preparing dimethyldithiocarbonate from dimethyl disulfide in a reactor and under the following conditions:
Temperature: 160° C.,
Carbon monoxide pressure: 4 MPa.

Example 1

A solution of dimethyl disulfide (22.43 ml; 250 mmol) was diluted in anhydrous toluene (500 ml). After elimination of the air using a vacuum pump, the mixture was stirred at 200 rpm, brought to 160° C. and placed under a carbon monoxide pressure (4 MPa) for 40 hours.

Example 2

Chlorotris(triphenylphosphine)rhodium (or RhCl(PPh$_3$)$_3$) having an oxidation state (I) (2.813 g; 3.0 mmol) and triphenylphosphine (1.732 g; 6.6 mmol) were diluted into a solution of dimethyl disulfide (22.43 ml; 250 mmol) diluted in anhydrous toluene (500 ml). After elimination of the air using a vacuum pump, the mixture was stirred at 200 rpm, brought to 160° C. and placed under a carbon monoxide pressure (4 MPa) for 40 hours.

Example 3

Chlorotris(triphenylphosphine)cobalt (or CoCl(PPh$_3$)$_3$) having an oxidation state (I) (3.689 g; 4.2 mmol) and triphenylphosphine (1.732 g; 6.6 mmol) were diluted into a solution of dimethyl disulfide (22.43 ml; 250 mmol) diluted in anhydrous toluene (500 ml). After elimination of the air using a vacuum pump, the mixture was stirred at 200 rpm, brought to 160° C. and placed under a carbon monoxide pressure (4 MPa) for 40 hours.

Example 4

Tetrakis(triphenylphosphine)palladium (or Pd(PPh$_3$)$_4$) having an oxidation state (0) (3.513 g; 3.0 mmol) and triphenylphosphine (1.732 g; 6.6 mmol) were diluted into a solution of dimethyl disulfide (22.43 ml; 250 mmol) diluted in anhydrous toluene (500 ml). After elimination of the air using a vacuum pump, the mixture was stirred at 200 rpm, brought to 160° C. and placed under a carbon monoxide pressure (4 MPa) for 40 hours.

The yield of the dimethyldithiocarbonate produced was determined, for each example after 3 hours, 20 hours and 40 hours of reaction, by gas chromatography on an Agilent DB1-ms 0.32 mm×60 m×5 µm column. The temperature gradient applied is 50° C. for 3 minutes, then 10° C. per minute up to 240° C., and 240° C. for 8 minutes. The detection was carried out with a thermal conductivity detector (TCD).

The results obtained are shown in Table 1 below.

TABLE 1

| | Catalyst evaluation | | | |
|---|---|---|---|---|
| Examples | Catalyst | Yield at 3 h | Yield at 20 h | Yield at 40 h |
| 1 (control) | — | 0% | 0% | 0% |
| 2 (comparative) | RhCl(PPh$_3$)$_3$ | 3.8% | 3.9% | 3.9% |
| 3 (comparative) | CoCl(PPh$_3$)$_3$ | 3.5% | 3.7% | 3.9% |
| 4 (invention) | Pd(PPh$_3$)$_4$ | 3.9% | 5.0% | 5.4% |

The results presented in Table 1 show that the yield of the dimethyl disulfide carbonylation reaction is improved, when the catalyst is tetrakis(triphenylphosphine)palladium having an oxidation state (0).

Evaluation of the Additional Ligands

The additional ligands 1,2-bis(diphenylphosphino)ethane (or dppe), 1,5-bis(diphenylphosphino)pentane (or dpppentane) and 1,1'-bis(diphenylphosphino)ferrocene (or dppf) are evaluated in a reaction for preparing dimethyldithiocarbonate from dimethyl disulfide and tetrakis(triphenylphosphine)palladium with an oxidation state (0) in a reactor and under the following conditions:
Temperature: 160° C.,
Carbon monoxide pressure: 4 MPa.

Example 5

Tetrakis(triphenylphosphine)palladium having an oxidation state (0) (3.513 g; 3.0 mmol) and 1,2-bis(diphenylphosphino)ethane (3.076 g; 7.0 mmol) were diluted into a solution of dimethyl disulfide (22.43 ml; 250 mmol) diluted in anhydrous toluene (500 ml). After elimination of the air using a vacuum pump, the mixture was stirred at 200 rpm, brought to 160° C. and placed under a carbon monoxide pressure (4 MPa) for 40 hours.

Example 6

Tetrakis(triphenylphosphine)palladium having an oxidation state (0) (3.513 g; 3.0 mmol) and 1,5-bis(diphenylphosphino)pentane (2.782 g; 7.0 mmol) were diluted into a solution of dimethyl disulfide (22.43 ml; 250 mmol) diluted in anhydrous toluene (500 ml). After elimination of the air using a vacuum pump, the mixture was stirred at 200 rpm, brought to 160° C. and placed under a carbon monoxide pressure (4 MPa) for 40 hours.

Example 7

Tetrakis(triphenylphosphine)palladium having an oxidation state (0) (3.513 g; 3.0 mmol) and 1,1'-bis(diphenylphosphino)ferrocene (3.871 g; 7.0 mmol) were diluted into a solution of dimethyl disulfide (22.43 ml; 250 mmol) diluted in anhydrous toluene (500 ml). After elimination of the air using a vacuum pump, the mixture was stirred at 200 rpm, brought to 160° C. and placed under a carbon monoxide pressure (4 MPa) for 40 hours.

The yield of the dimethyldithiocarbonate produced was determined, for each example after 3 hours, 20 hours and 40 hours of reaction, by gas chromatography on an Agilent DB1-ms 0.32 mm×60 m×5 μm column. The temperature gradient applied is 50° C. for 3 minutes, then 10° C. per minute up to 240° C., and 240° C. for 8 minutes. The detection was carried out with a thermal conductivity detector (TCD).

The results obtained are shown in Table 2 below.

TABLE 2

| | Evaluation of the additional ligands | | | |
|---|---|---|---|---|
| Examples | Additional ligand | Yield at 3 h | Yield at 20 h | Yield at 40 h |
| 5 (Invention) | dppe | 7.5% | 7.8% | 8.0% |
| 6 (Invention) | dpppentane | 7.3% | 7.8% | 8.2% |
| 7 (Invention) | dppf | 8.2% | 8.6% | 9.0% |

Evaluation of the Initial Concentration of Dimethyl Disulfide

The initial concentration of dimethyl disulfide is evaluated in a reaction for preparing dimethyldithiocarbonate and in the presence of tetrakis(triphenylphosphine)palladium having an oxidation state (0) and 1,1'-bis(diphenylphosphino)ferrocene, in anhydrous toluene. The reaction is carried out in a reactor and under the following conditions:
Temperature: 130° C.,
Carbon monoxide pressure: 15 MPa.

Example 8

Tetrakis(triphenylphosphine)palladium (or Pd(PPh$_3$)$_4$) having an oxidation state (0) (0.35 g; 0.31 mmol) and 1,1'-bis(diphenylphosphino)ferrocene (0.5 g; 0.90 mmol) were diluted into a solution of dimethyl disulfide (26.7 ml; 300 mmol) diluted in anhydrous toluene (made up to 60 ml). After elimination of the air using a vacuum pump, the mixture was stirred at 1200 rpm, brought to 130° C., and placed under a carbon monoxide pressure (15 MPa) for 70 hours.

Example 9

Tetrakis(triphenylphosphine)palladium (or Pd(PPh$_3$)$_4$) having an oxidation state (0) (0.35 g; 0.31 mmol) and 1,1'-bis(diphenylphosphino)ferrocene (0.5 g; 0.90 mmol) were diluted into a solution of dimethyl disulfide (2.67 ml; 30 mmol) diluted in anhydrous toluene (made up to 60 ml). After elimination of the air using a vacuum pump, the mixture was stirred at 1200 rpm, brought to 130° C., and placed under a carbon monoxide pressure (15 MPa) for 70 hours.

For these Examples 8 and 9, the dimethyldithiocarbonate yields were determined by gas chromatography on an Agilent DB1-ms 0.32 mm×60 m×5 μm column after 24, 42 and 70 h. The temperature gradient applied is 50° C. for 3 minutes, then 10° C. per minute up to 240° C., and 240° C. for 8 minutes. The detection was carried out with a thermal conductivity detector (TCD).

The results obtained are shown in Table 3 below.

TABLE 3

| Evaluation of the initial concentration of dimethyl disulfide | | | |
|---|---|---|---|
| Examples | Yield at 24 h | Yield at 42 h | Yield at 70 h |
| 8 (Invention) | 21.7% | 23.3% | 24.1% |
| 9 (Invention) | 57.1% | 65.3% | 71.9% |

The invention claimed is:
1. A process for preparing a S,S'-dialkyldithiocarbonate, comprising:
reacting in the presence of carbon monoxide:
a dialkyl disulfide chosen from formula (I) below, and mixtures thereof:

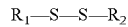

$R_1$—S—S—$R_2$ wherein $R_1$ and $R_2$, which may be identical or different, are a $C_1$-$C_{12}$ alkyl group,
a catalyst comprising a metal chosen from nickel, palladium and platinum,
and
optionally in the presence of a solvent or of a mixture of solvents.

2. The process according to claim 1, wherein $R_1$ and $R_2$ are identical and are a $C_1$-$C_4$ alkyl group.

3. The process according to claim 1, wherein the catalyst comprises palladium.

4. The process according to claim 1, wherein the number of moles of the catalyst is between 0.1 and 3 mol %, relative to the total number of moles of the dialkyl disulfide.

5. The process according to claim 1, wherein the reacting step is carried out under a total carbon monoxide pressure of between 1 and 20 MPa.

6. The process according to claim 1, wherein the reacting step further comprises the addition, to the reaction medium, of at least one additional ligand.

7. The process according to claim 6, wherein the additional ligand(s) are chosen from triphenylphosphine, 1,2-bis(diphenylphosphino)ethane, 1,5-bis(diphenylphosphino)pentane, 1,1'-bis(diphenylphosphino)ferrocene, 1,3-diisopropylimidazolium tetrafluoroborate, 1,4-bis(diphenylphosphino)butane, carbon monoxide, and mixtures thereof.

8. The process according to claim 6, wherein the number of moles of the additional ligand(s) is between 0.1 and 6 mol %, relative to the total number of moles of the dialkyl disulfide.

9. The process according to claim 2, wherein $R_1$ and $R_2$ are each a methyl group.

10. The process according to claim 3, wherein the catalyst is tetrakis(triphenylphosphine)palladium.

* * * * *